United States Patent
Klein et al.

[11] Patent Number: 5,922,020
[45] Date of Patent: Jul. 13, 1999

[54] TUBULAR PROSTHESIS HAVING IMPROVED EXPANSION AND IMAGING CHARACTERISTICS

[75] Inventors: Enrique J. Klein, Los Altos; Anthony P. Widdershoven, Citrus Heights, both of Calif.

[73] Assignee: Localmed, Inc., Palo Alto, Calif.

[21] Appl. No.: 08/691,661

[22] Filed: Aug. 2, 1996

[51] Int. Cl.⁶ .................................................. A61F 2/06
[52] U.S. Cl. ........................ 623/1; 623/12; 606/194; 606/198
[58] Field of Search .................... 623/1, 11, 12; 606/108, 191, 194, 195, 198; 604/96, 104

[56] References Cited

U.S. PATENT DOCUMENTS

| | | |
|---|---|---|
| 4,886,062 | 12/1989 | Wiktor . |
| 5,019,090 | 5/1991 | Pinchuk .................................... 606/194 |
| 5,496,365 | 3/1996 | Sgro ............................................ 623/1 |
| 5,514,154 | 5/1996 | Lau et al. .................................. 606/195 |
| 5,556,414 | 9/1996 | Turi ............................................ 606/198 |
| 5,562,697 | 10/1996 | Christiansen ............................. 606/191 |
| 5,569,295 | 10/1996 | Lam . |
| 5,591,197 | 1/1997 | Orth et al. . |
| 5,593,442 | 1/1997 | Klein ........................................... 623/12 |
| 5,607,445 | 3/1997 | Summers .................................. 606/198 |

FOREIGN PATENT DOCUMENTS

| | | | |
|---|---|---|---|
| 0 662 307 | 7/1995 | European Pat. Off. .......... | A61F 2/06 |
| 0 679 372 | 11/1995 | European Pat. Off. ........ | A61B 19/00 |
| 95/26695 | 10/1995 | WIPO ........................................ | 623/1 |

Primary Examiner—Mickey Yu
Assistant Examiner—Francis K. Cuddihy
Attorney, Agent, or Firm—Townsend and Townsend and Crew LLP

[57] ABSTRACT

A radially expansible lumenal prosthesis comprises one or more body segments which include struts and hinge regions between the struts. Certain of the hinge regions are weakened relative to others so that the expansion characteristics of the prosthesis may be programmed. In particular, by distributing the weakened hinge regions circumferentially about the body segment, uniform expansion of the prosthesis can be improved, even when the prosthesis is only partially deployed.

15 Claims, 11 Drawing Sheets

TUBULAR PROSTHESIS HAVING IMPROVED EXPANSION AND IMAGING CHARACTERISTICS

BACKGROUND OF THE INVENTION

1. Field of the Invention

The present invention relates generally to the structure of radially expansible lumenal prostheses, including stents and grafts. More particularly, the present invention relates to the structure of prostheses having controlled expansion characteristics and controlled radiopacity.

Lumenal prostheses are provided for a variety of medical purposes. For example, lumenal stents can be placed in various body lumens, such as blood vessels, the ureter, the urethra, the biliary tract, and the gastrointestinal tract, for maintaining patency. Such stents are particularly useful for placement in pre-dilated atherosclerotic sites in blood vessels. Lumenal grafts can be placed in blood vessels to provide support in diseased regions, such as abdominal and other aneurysms.

Lumenal stents and other prostheses are available in a wide variety of configurations, including helical coils, rolled tubular sleeves, serpentine rings, zig-zag rings, expansible box constructions, and the like. Each of these configurations may also be provided as either a self-expanding prothesis, typically being formed from an alloy displaying superelastic and/or shape memory properties, such as nickel titanium, or as a malleable prosthesis which is deployed by internal expansion of a balloon to radially expand the prosthesis structure.

Of particular interest to the present invention, are serpentine, zig-zag, and box stents which comprise a plurality of strut elements joined by malleable or plastically deformable hinge regions. Such prostheses are expanded by applying a radially outward internal force within a lumen of the prosthesis, typically by expanding a balloon catheter therein. As a result of such radially expansive forces, the hinge regions yield and the struts open away from each other to increase the diameter and peripheral dimension of the prostheses. While stents and other prostheses having such structures have been quite successful, they can suffer from non-uniform opening characteristics, as described in more detail below.

An exemplary prosthesis construction is shown in FIG. 1, where a serpentine stent 10 comprises struts 12 joined by hinge regions 14. The particular stent 12 illustrated includes a total of twelve struts 12 joined by twelve hinge regions 14, with six hinge regions being disposed at each end of the stent. Ideally, as the stent 12 is expanded by a balloon, each of the hinge regions 12 will open simultaneously at an equal rate so that the angles between adjacent struts 12 remain equal at all times during expansion. Unfortunately, even very small differences in the mechanical characteristics of the different hinge regions 12 can result in significantly different opening rates, as discussed below. Additionally, when a stent is deployed by a pre-folded balloon, certain internal surfaces of the stent may experience greater tangential forces than experienced by other surfaces, causing an uneven expansion.

FIGS. 2 and 3 illustrate stent 10 in a "rolled-out" view. FIG. 2 shows the stent in its non-expanded configuration prior to deployment. FIG. 3 shows the stent in a typical configuration after partial opening as a result of internal balloon expansion. The uneven pattern of FIG. 3 will result when hinge regions 14a are mechanically stronger than hinge regions 14b, resulting in hinge regions 14b opening more readily than hinge regions 14a. A similarly uneven expansion pattern may also result from non-uniform tangential forces between the balloon and the interior surfaces of the stent, or from a combination of these forces and differences in the strengths of the hinge regions. It will be appreciated that such non-uniformity results in a very poor distribution of support about the periphery of the body lumen being treated. As illustrated in FIG. 3, approximately one-half of the periphery of the body lumen would be supported by the four struts 12b, while the remaining one-half of the periphery would be supported by eight struts 12a. While the poor distribution of stent opening may be at least partially reduced as the stent 10 is further expanded, in many cases the stent 10 will only be partially opened after the deployment is complete. In such cases, the non-uniform strut distribution pattern will be a significant problem.

A separate problem in stent construction and deployment relates to the ability to detect the stent fluoroscopically during the deployment procedure. Stents composed of nickel titanium alloys and other radiopaque materials can be readily observed fluoroscopically if the cross-sections of their components are sufficiently large. If the stent is highly radiopaque, however, the stent itself, even in its expanded condition, can interfere with subsequent fluoroscopic examination of the treated area to confirm that the body lumen remains patent. In contrast, stainless steel and other common stent materials are generally radiolucent, i.e. they permit fluoroscopic examination therethrough. Such stents are advantageous since they do not prevent subsequent fluoroscopic examination of the treated region of the body lumen. They are, however, much more difficult to position accurately and usually require attachment of a separate radiopaque marker(s).

For these reasons, it would be desirable to provide improved stents and other lumenal protheses. In particular, it would be desirable to provide radially expansible stents and prostheses comprising strut and hinge regions, where the opening characteristics of the struts may be "programmed" to assure uniformity. Additionally, it would be desirable to provide improved stents and other prostheses having radiopacity characteristics which permit both tracking during deployment and subsequent visualization of the treated lumen after deployment. The present invention will provide at least some of the desired improvements.

2. Description of the Background Art

EP 662 307 describes an expansible stent having serpentine elements having regions with varying degrees of curvature to provide controlled expansion characteristics. EP 679 372 describes an expansible stent which is plated with a radiopaque material at each end to enhance fluoroscopic visibility.

Copending application Ser. No. 08/463,166, filed on Jun. 5, 1996, describes a radially expansible stent which could employ the weakened hinge regions of the present invention to control deployment. The full disclosure of this application is incorporated herein by reference.

SUMMARY OF THE INVENTION

The present invention provides improved radially expansible tubular prostheses and methods for their endolumenal placement within body lumens, particularly blood vessels. The prostheses may be in the form of stents, intended for maintaining lumenal patency, or may be in the form of grafts, intended for protecting or enhancing the strength of the lumenal wall. The prostheses of the present invention will be plastically deformable or malleable and radially expansible by the application of a radially outward internal force, typically applied by a balloon catheter expanded within a lumen of the prosthesis.

In a first aspect of the present invention, the radially expansible tubular prosthesis comprises at least one serpentine, zig-zag, or box element having struts joined together by hinge regions which yieldably open in response to a radially outwardly directed internal force. Selected ones of the hinge regions are weakened relative to others so that the weakened hinge regions open before the other (non-weakened or strengthened) hinge regions. Usually, it will sufficient to provide only two "groups" of hinge regions, (i.e., one group which is weakened relative to the other) but it will also be possible to provide three, four, or more different groups of hinge regions, each group programmed to open in response to successively greater expansion forces. By properly distributing the weakened and non-weakened hinge regions about the tubular prosthesis, usually but not necessarily distributing the weakened regions evenly about the periphery, the stent can be "programmed" to open in a generally uniform manner. That is, opening of the stent will not be confined to a limited region in one portion or on one side of the stent.

Exemplary serpentine (or zig-zag) elements will usually comprise a plurality of struts having substantially equal lengths joined together in a reversing pattern. The reversing pattern will typically comprise repeating S-shaped hinge regions or repeating Z-shaped hinge regions. The latter pattern is commonly referred to a zig-zag stent.

Box elements will typically comprise a plurality of struts and hinge regions joined in a rectangular pattern, where the rectangle opens to a diamond or lozenge pattern as the prosthesis is expanded. Preferably, the box elements each include four struts joined by four hinges. The struts are arranged in two colinear pairs, each with one hinge region therebetween. The two pairs of struts are then joined together in parallel, with a single hinge at each end. Box elements are attached to each other at or near the hinge regions between the colinear struts, with the expansion force being applied through these hinge regions. In this way, the box elements open into the diamond or lozenge pattern as the prosthesis is radially expanded.

In further preferred aspects of the present invention, the weakened hinge regions are disposed between the ends of adjacent pairs of parallel struts. In this way, the hinge region will act as the center of deflection (or in some cases centers as described in detail below) about which the two adjacent struts open as the prosthesis is expanded. In other cases, however, the weakened hinge regions may be disposed between adjacent ends of pairs of colinear struts. In such cases, the struts will usually be initially straight (axially aligned) and will deform about a hinge region between the struts as the prosthesis is opened. The serpentine or zig-zag structures will typically comprise a plurality of parallel, adjacent struts which are joined by hinge regions between pairs of struts on alternating sides of the prosthesis element. By peripherally disposing weakened hinge regions evenly about the tubular prosthesis (as described in much greater detail below), a generally uniform pattern of opening of the prosthesis can be assured. Box elements will generally comprise at least four struts, with the inner ends of the struts being joined in a colinear manner and the outside ends of the struts being joined in a parallel manner. Such a hinge pattern will provide opening of the original rectangular structure into a diamond pattern. The tubular prosthesis structures will generally include a plurality of circumferentially spaced-apart box elements joined near the center hinge regions. By appropriately locating weakened hinge regions in particular ones of the box elements, a generally uniform pattern of opening can be provided.

The phrase "weakened hinge region" refers to the relative stiffness or pending resistance of one hinge region to another. Typically, all hinge regions will be "weak" relative to the struts. That is, as a prosthesis is expanded, the struts will resist deformation and remain essentially straight while deflecting relative to each other about the hinge regions. The present invention further provides that the "weakened hinge regions," i.e., those that are more bendable than others of the hinge regions, will deflect first so that initial expansion occurs in selected regions of the prosthesis where the weakened hinge regions are present. In particular, the pattern of weakened hinge regions will usually be selected so that a plurality of circumferentially spaced-apart regions (which are preferably uniformly distributed about the periphery) are provided about the stent, which regions initially opened to provide for more uniform opening characteristics as the prosthesis is deployed.

The relative weakness and strength of the various hinge regions can be provided in a variety of ways. For example, it may be possible to selectively treat individual hinge regions with heat, radiation, mechanical working, or combinations thereof, so that the mechanical characteristics of the hinge region are altered, i.e., so that selected hinge regions will bend or deflect with a greater or lesser expansion force than others of the hinge regions. Preferably, however, the strength of the hinge regions will be programmed by controlling the relative cross-sectional dimensions of the different hinge regions. Usually, the weakened hinge regions will have cross-sectional dimensions which are selected so that the force required to "open" the hinge is less than that required for other non-weakened hinge regions. Usually, the hinge will have a section in which the height in the radial direction remains constant (i.e. it will be the same as the remainder of the hinge, struts, and other portions of the tubular prosthesis) while the width in the circumferential direction will be reduced by up to 30% relative to the non-weakened hinge regions. It will be appreciated, of course, that "weakened" and "non-weakened" are relative terms, and it would be possible to augment or increase the width of the non-weakened regions relative to the weakened regions. It will also be possible to provide two or more discrete narrowings within a single hinge region, or to provide one or more narrowings in the regions of the struts immediately adjacent to the hinge regions. Specific designs for such weakened hinge regions will be presented in detail below.

In a particularly preferred embodiment, the hinge regions will have a rectangular cross-sectional geometry where the width is the broadest dimension and is aligned circumferentially within the tubular prosthesis. Typically, the width of the weakened hinge region will be reduced by from about 20% to 30% relative to the widths of the other, non-weakened hinge regions. Since bending will occur about a radial axis which is normal to the width dimension, the moment of inertia about the bending axis will be directly proportional to the third power of the width. Thus, even very small differences in width will provide a significant difference in bending strength. Moreover, the width of the hinge regions may be readily controlled during fabrication by adjusting the width. This will be a particularly convenient method when the prosthesis is formed by laser, EDM, or photolithographic etching of a tubular material.

In a specific aspect of the present invention, the hinge regions may be defined by cutting notches or voids into structural material of the hinge region. For example, V-shaped notches may be cut into the hinge region on the side which undergoes compression during opening of the hinge. Alternatively, a C-shaped void may be cut into the same side of the hinge region. In both cases, the hinge region will include opposed stops which will engage each other as the hinge region is opened to a predefined angle, typically from 20° to 40°. Once the opposed stops engage each other, the hinge region will be substantially strengthened so that further opening of the hinge is inhibited. By properly selecting the bending strengths of the other hinge regions, the prosthesis can be programmed so that the other group(s) of hinge regions will then start or continue to open after opening of the first group of hinge regions has been inhibited by the opposed stops.

In a second aspect of the present invention, the prostheses described above may be delivered to a body lumen by applying a radially outward force within a lumen of the prosthesis to radially expand the prosthesis. In particular, the weakened hinge regions will yield before the other hinge regions, as described above, to enhance uniformity of opening.

In a third aspect of the present invention, a radially expansible tubular prosthesis comprises an expansible tubular shell, wherein substantially the entire inner and/or outer surface of the shell is plated with a layer of radiopaque material. Typically, the tubular prosthesis will be composed of stainless steel and the radiopaque material will be selected from the group consisting of gold, platinum, platinum/iridium, tungsten, tantalum, or the like. Preferably, the radiopaque material will be plated to a thickness selected to enhance fluoroscopic visibility of the entire length of the prosthesis while permitting sufficient fluoroscopic translucence so that the lumen inside the prosthesis may be inspected fluoroscopically. In the case of gold, the layer will preferably be applied in a thickness in a range from 0.01 mm to 0.03 mm.

In a fourth aspect of the present invention, the radially expansible tubular prostheses having the plated radiopaque layers as described above may be delivered while fluoroscopically viewing a target region within a body lumen. In prosthesis is positioned in the body lumen while observing the fluoroscopic image of the entire prosthesis. The prosthesis is then deployed at the target site. Typically, such prosthesis will be malleable and composed of stainless steel, but the method may also apply to superelastic, shape memory alloy, and other self-deploying prostheses.

DESCRIPTION OF THE SPECIFIC EMBODIMENT

Figure 1:
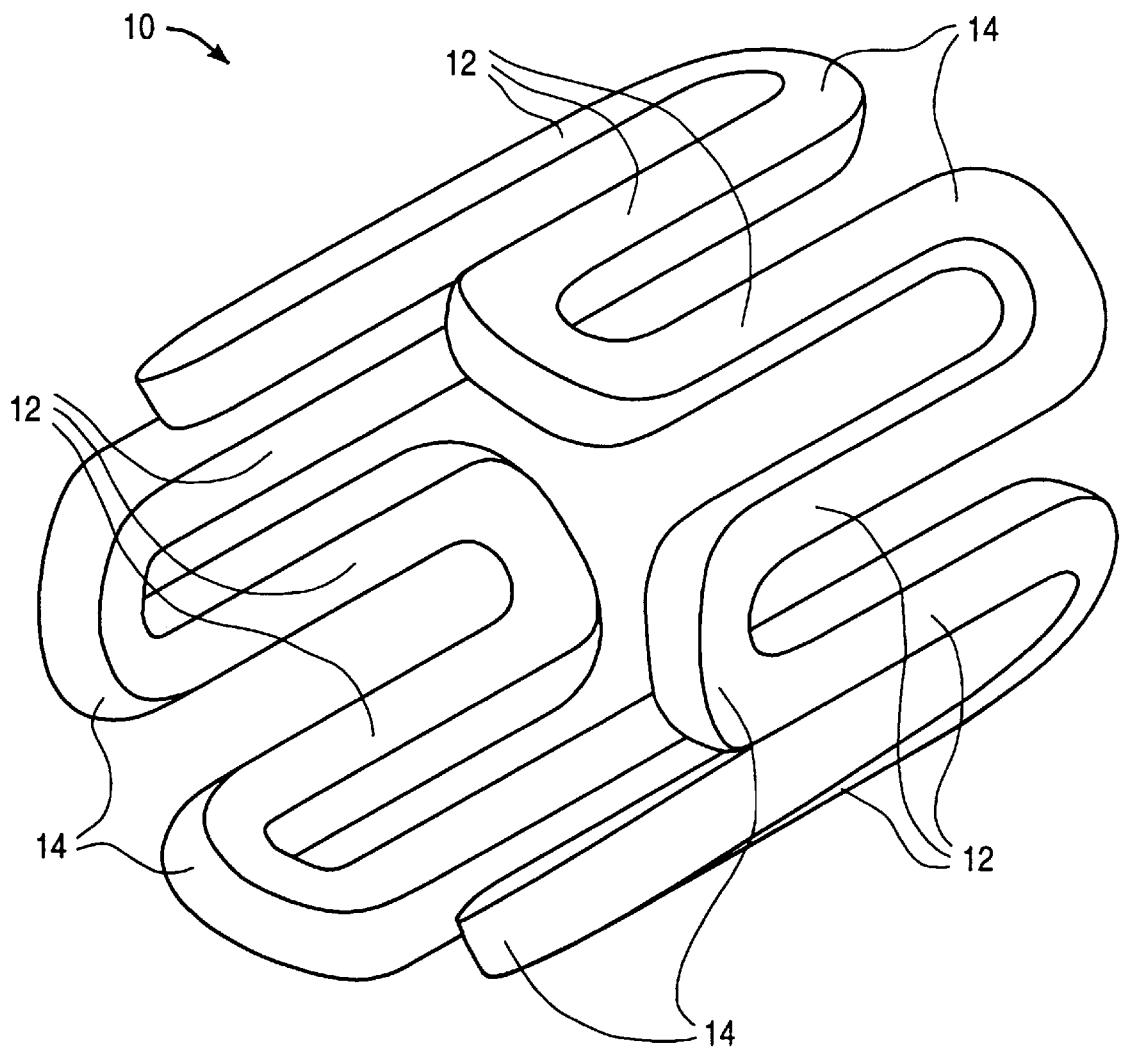
FIG. 1 is a perspective view of a prior art serpentine stent.
Figure 2:
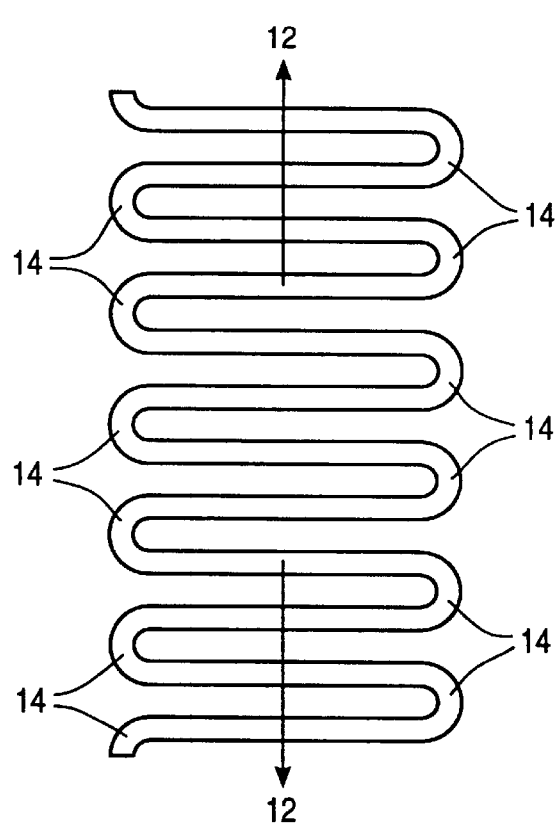
FIG. 2 illustrates the serpentine stent of FIG. 1 prior to expansion in a "rolled-out" view.

The present invention provides devices and methods for the endolumenal placement of prostheses, particularly within the vascular system for the treatment of cardiovascular disease, such as vascular stenoses, dissections, aneurysms, and the like. The apparatus and methods, however, are also useful for placement in other body lumens, such as the ureter, urethra, biliary tract, gastrointestinal tract and the like, for the treatment of other conditions which may benefit from the introduction of a reinforcing or protective structure within the body lumen.

The prostheses will be placed endolumenally. As used herein, "endolumenally" will mean placement by percutaneous or cutdown procedures, wherein the prosthesis is translumenally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the coronary arteries.

A lumenal prosthesis according to the present invention will comprise at least one radially expansible, usually tubular body segment. By "radially expansible," it is meant that the body segment can be converted from a small diameter configuration (used for endolumenal placement) to a radially expanded, usually cylindrical, configuration which is achieved when the prosthesis is implanted at the desired target site. The prosthesis will be non-resilient, e.g., malleable, thus requiring the application of an internal force to expand it at the target site. Typically, the expansive force can be provided by a balloon catheter, such as an angioplasty balloon for vascular procedures.

The dimensions of the lumenal prosthesis will depend on its intended use. Typically, the prosthesis will have a length in the range from 0.5 cm to 10 cm, usually being from about 1 cm to 5 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 30 mm, preferably being in the range from about 2.5 mm to 15 mm for vascular applications. The body segments may be formed from conventional malleable materials used for body lumen stents and grafts, typically being formed from metals, such as 300 series stainless steel.

The body segments of the tubular prostheses will comprise a plurality of struts joined together by hinge regions. Usually, the struts and hinge regions will be formed into conventional patterns of the type previously employed in stents and grafts. For example, the struts and hinge regions may be formed into serpentine patterns, including both S-shaped serpentine rings, such as those illustrated in EP 679,372, as well as Z-shaped or zig-zag stents, such as those illustrated in U.S. Pat. No. 5,292,331. The body segments may also comprise box elements, such as those utilized in the Palmaz stent, which is presently being manufactured by Johnson and Johnson Interventional Systems, and which is generally described in U.S. Pat. No. 4,776,337.

Figure 3:
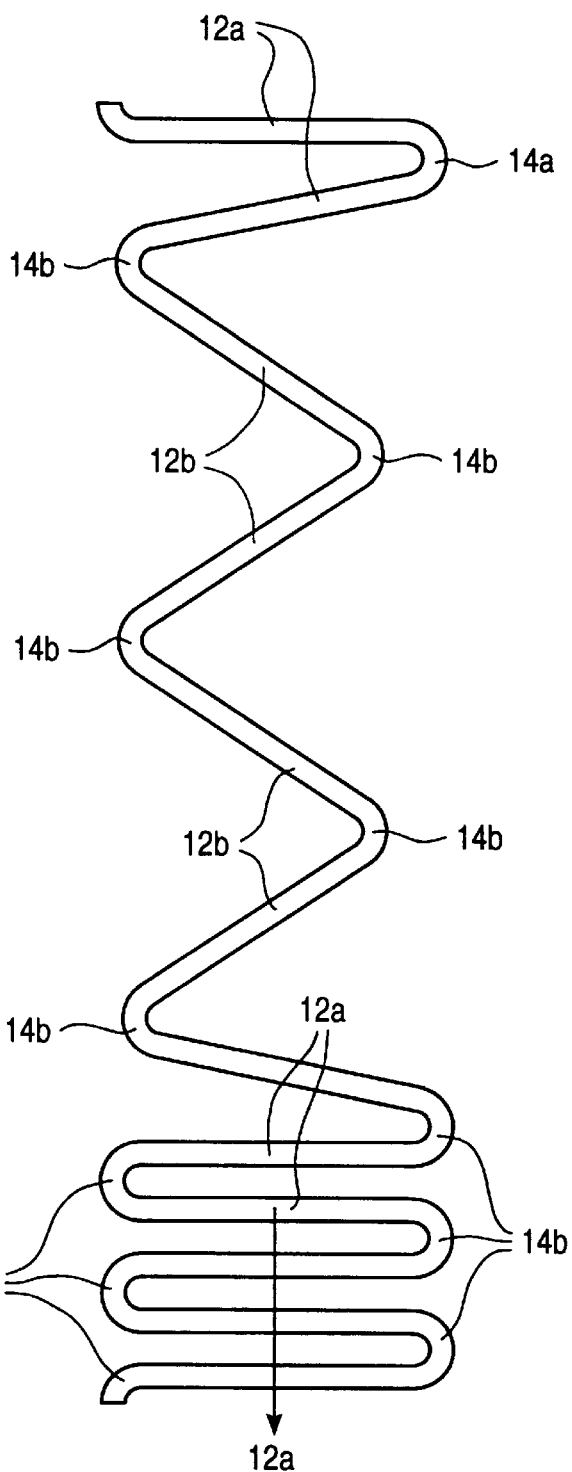
FIG. 3 illustrates the serpentine stent of FIG. 1 after partial expansion in a "rolled-out" view.

The present invention provides improvements over such conventional prosthesis structures by controlling the order of expansion of different circumferentially spaced-part regions of the prostheses. In particular, radial expansion of any circumferential portion of the prosthesis is controlled by adjusting the strength or weakness of at least some of the hinge region(s) located in that region of the prosthesis. A plurality of circumferentially spaced-apart regions of the prosthesis will have hinge regions which are weakened relative to the hinge regions in other portions of the prosthesis. By distributing these weakened hinge regions equally about the circumference of the prosthesis, the uniform pattern of expansion can be provided. Such uniformity is particularly desirable when a stent may become implanted after only partial expansion. If expansion of the stent is not uniformly distributed, as illustrated in FIG. 3 discussed above, support to a portion of the surrounding lumenal wall may be significantly compromised. The present invention ensures against such poor distribution of the supporting struts of the prosthesis after expansion.

Figure 4:
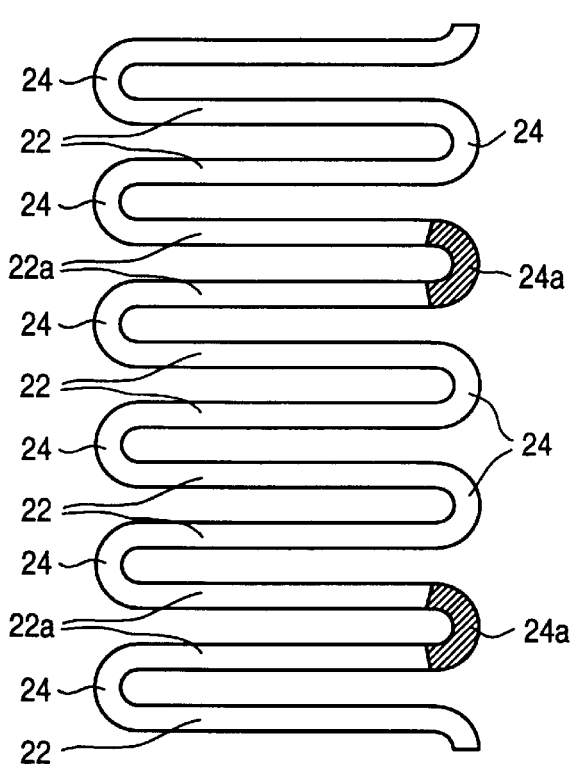
FIG. 4 is a "rolled-out" view of a serpentine stent similar to that illustrated in FIGS. 1–3, modified according to the principles of the present invention.
Figure 5:
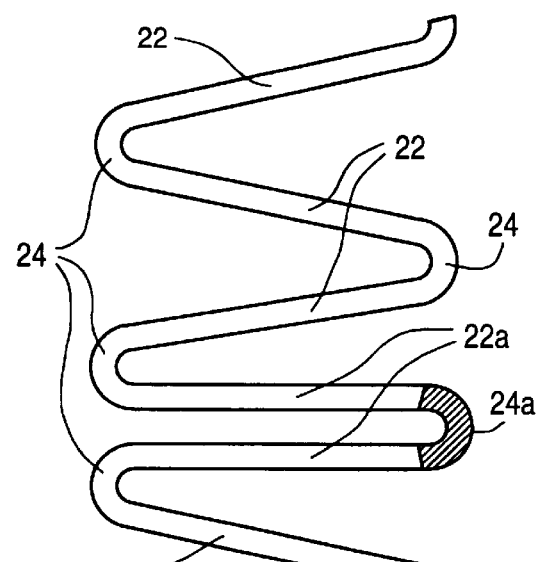
FIG. 5 is a "rolled-out" view of the stent of FIG. 4 after partial deployment.
Figure 6:
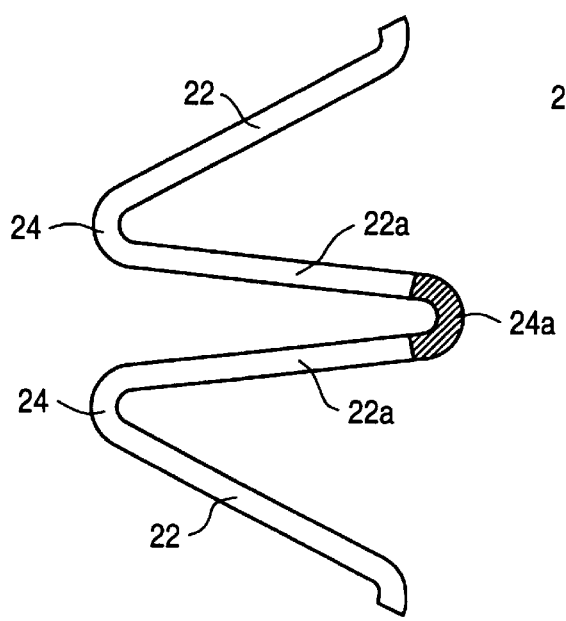
FIG. 6 is a detailed "rolled-out" view of a portion of the stent of FIGS. 4 and 5, after full deployment.

Referring now to FIGS. 4–6, a first exemplary embodiment of a stent 20 constructed in accordance with the present invention will be described. The stent 20 is similar to prior art stent 10 and includes a plurality of struts 22 joined at the respective ends by hinge regions 24. The stent 20, however, is modified so that ten of the hinge regions 24 are weakened relative to a pair of the hinge regions 24a. The hinge regions 24a are shaded and may have an increased width or other structural modification, as discussed generally above, so that a substantially greater radial expansion force is required to open the immediately adjacent struts 22a than the non-adjacent struts 22. It must be understood that the nature of the structural differences between the relatively weak hinge regions 22 and the relatively strong hinge regions 22a is not critical. It is necessary only that the hinge regions be modified in some way so that the adjacent struts 22 and 22a open in the desired order, i.e. with the struts 22a adjacent the stronger hinge regions 24a opening after the struts 22 adjacent the weakened hinge regions 22.

As a result of the pattern of strong hinge regions 24a and weakened hinge regions 24, partial expansion of the stent 20 results in the pattern shown in FIG. 5. There, it can be seen that by providing only two hinge regions which are strength- ened relative to the remaining hinge regions, four of the twelve struts 22 are inhibited from opening while an additional four of the struts are permitted to open only partially. Thus, at a point where the stent is approximately one-half open, the entire stent 20 will have a relatively uniform pattern of opening. Compare FIG. 5 with FIG. 3. As the stent 20 is further expanded, struts 24a adjacent the relatively strengthened hinge regions 24a will open, as shown in FIG. 6.

The stent 20 may be fabricated from any small diameter tubing comprised of a desired material, e.g. stainless steel hypotube. The pattern of struts and hinges may be formed in the hypotube by conventional patterning techniques including laser cutting, sinker EDM, photolithography and the like. Suitable laser cutting techniques are described in U.S. Pat. No. 5,073,694, and suitable photolithographic fabrication techniques are described in U.S. Pat. No. 5,421,955, the full disclosures of which are incorporated herein by reference. Using such fabrication techniques, the relative widths of the hinge regions 24 (as well as the widths and shapes of the hinge regions in subsequent embodiments) may be precisely controlled.

Figure 7:
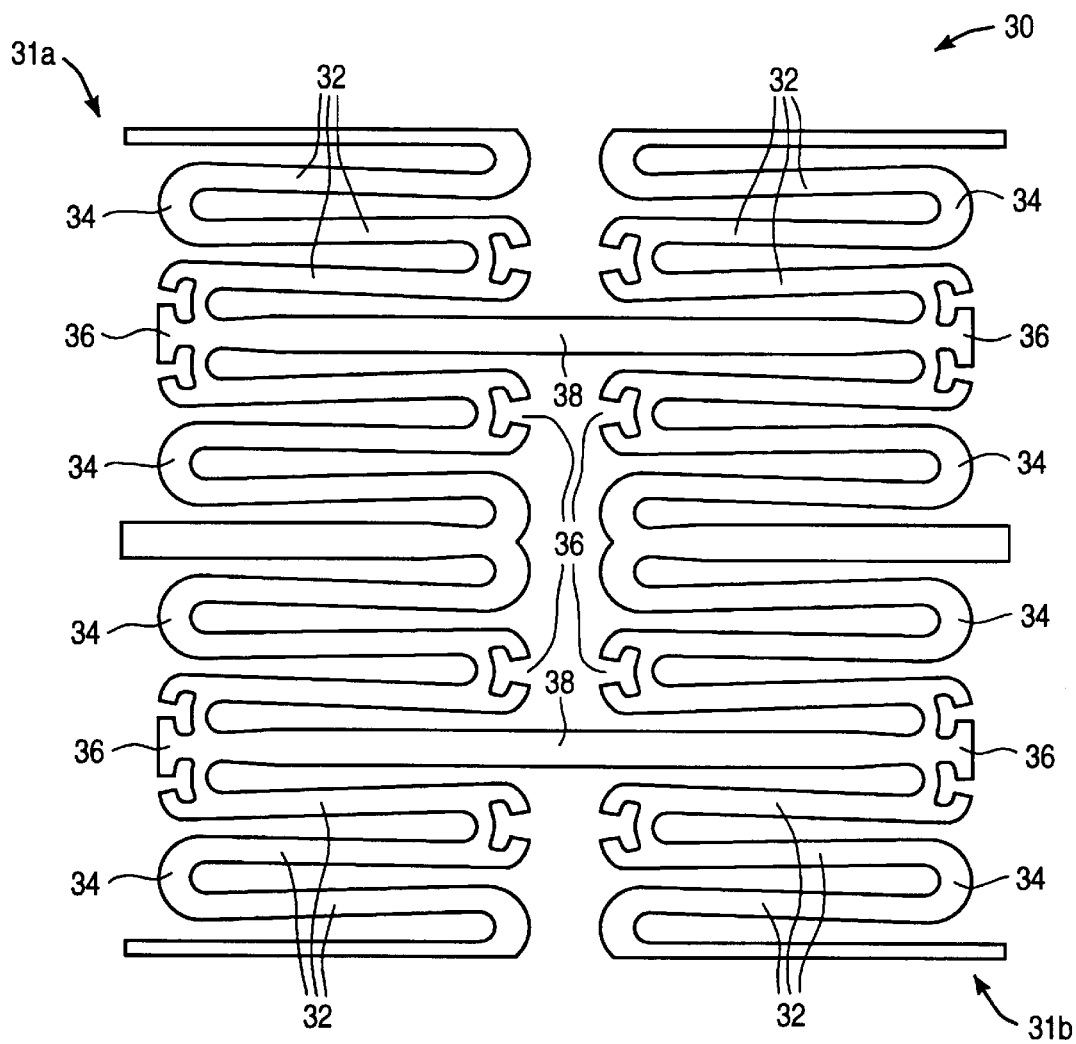
FIGS. 7 and 7A illustrates an alternative embodiment of a stent constructed in accordance with the principles of the present invention which employs hinge regions having opposed stop surfaces.
Figure 7A:
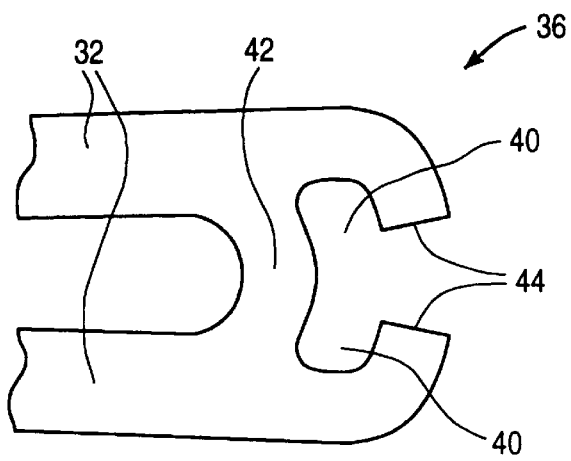
Figure 8:
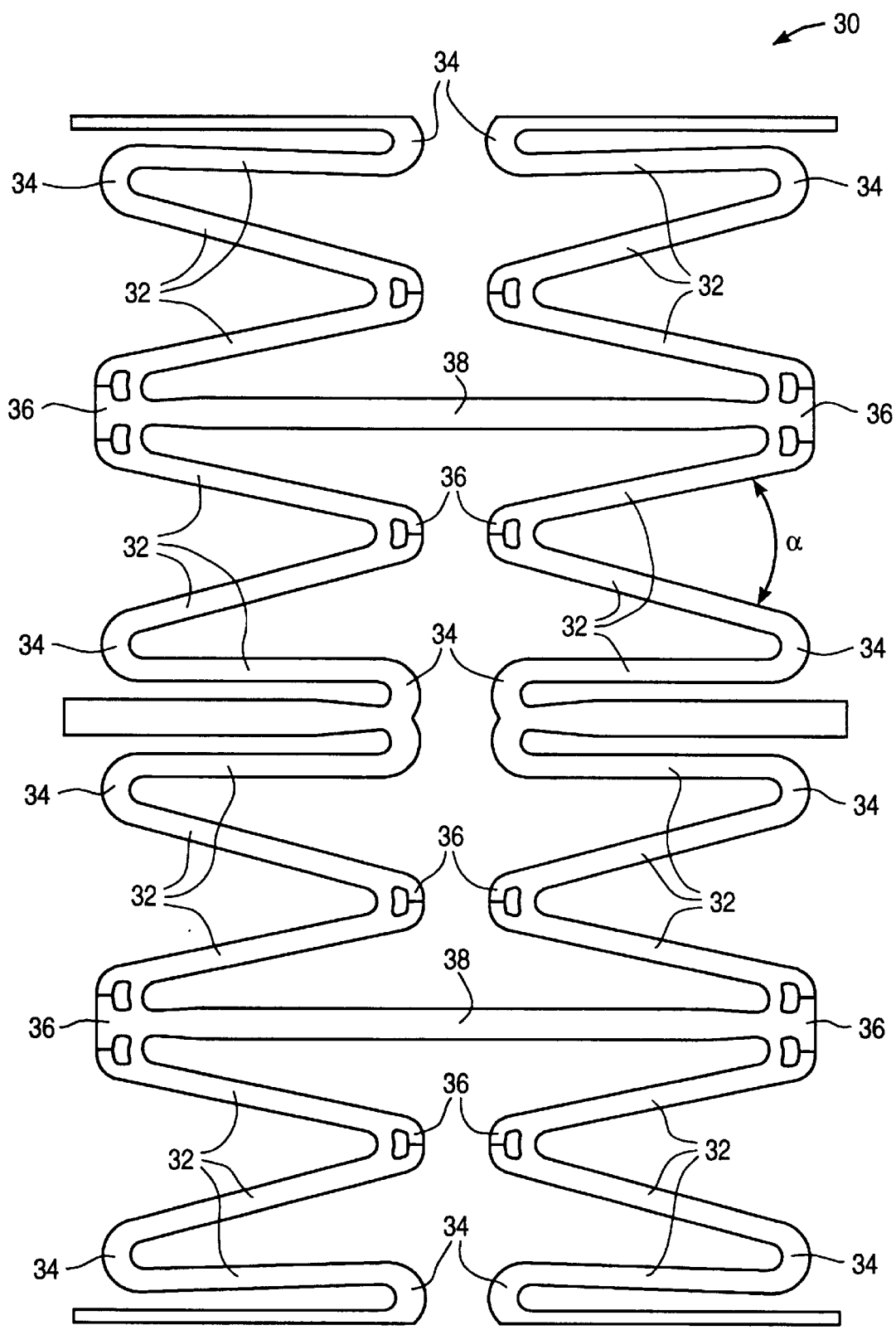
FIG. 8 illustrates the stent of FIG. 7 after partial deployment.
Figure 9:
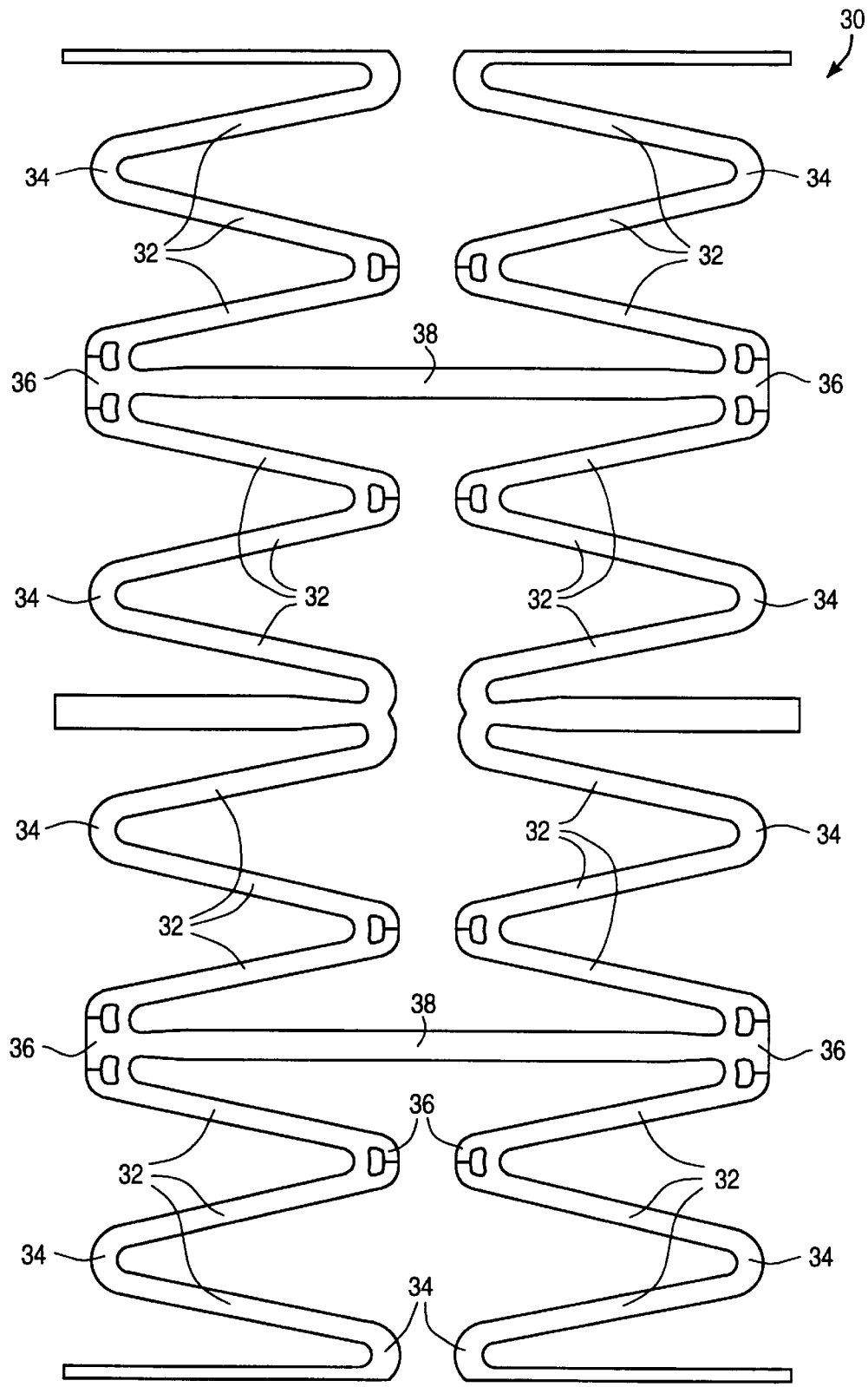
FIG. 9 illustrates the stent of FIGS. 7 and 8 after full deployment.

Referring now to FIGS. 7–9, a stent 30 employing an alternative pattern of struts 32 and hinges 34 and 36 is illustrated. Stent 30 comprises a pair of serpentine body segments 31a and 31b joined by beams 38, as illustrated. The hinge regions 36 are weakened relative to hinge regions 34 by formation of one or a pair of C-shaped cut-outs 40, as best illustrated in 57A. The cut-outs 40 reduce the width of the section 42 of hinge region 36 which joins the adjacent struts 32. The cut-outs 40 further define a pair of opposed stop surfaces 44 which are spaced-apart by a distance selected to permit the adjacent struts 32 to open by desired angle, typically in the range from 20° to 40°. After the stop surfaces 44 engage each other, further opening of the adjacent struts 32 will be inhibited, as illustrated in FIGS. 8 and 9.

The use of hinge regions 40 with opposed stop surfaces can be advantageous in several respects. First, it allows the weakened hinge regions to be quite weak during the initial expansion, but thereafter strengthened when a desired deployment configuration (i.e. strut deployment angle α as shown in FIG. 8) has been achieved. Thereafter, the hinge regions 36 may actually become strengthened relative to the other hinge regions 34. Thus, the remaining hinge regions 34 will open upon further radial internal expansion of the stent 30. In this way, a very uniform pattern of expansion of all hinge regions, both weakened and non-weakened may ultimately be achieved.

As illustrated in FIG. 8, the weakened hinge regions 36 will fully deploy prior to any significant opening of any of the non-weakened hinge regions 34. After the stop surfaces 44 have been engaged, however, the remaining hinge regions 34 will then open, providing a full deployment pattern as illustrated in FIG. 9.

Figure 10:
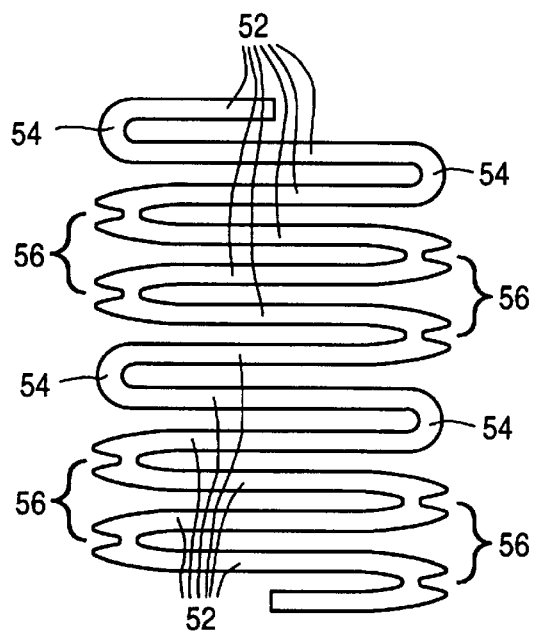
FIGS. 10 and 10A illustrates another embodiment of a stent constructed in accordance with the principles of the present invention.
Figure 11:
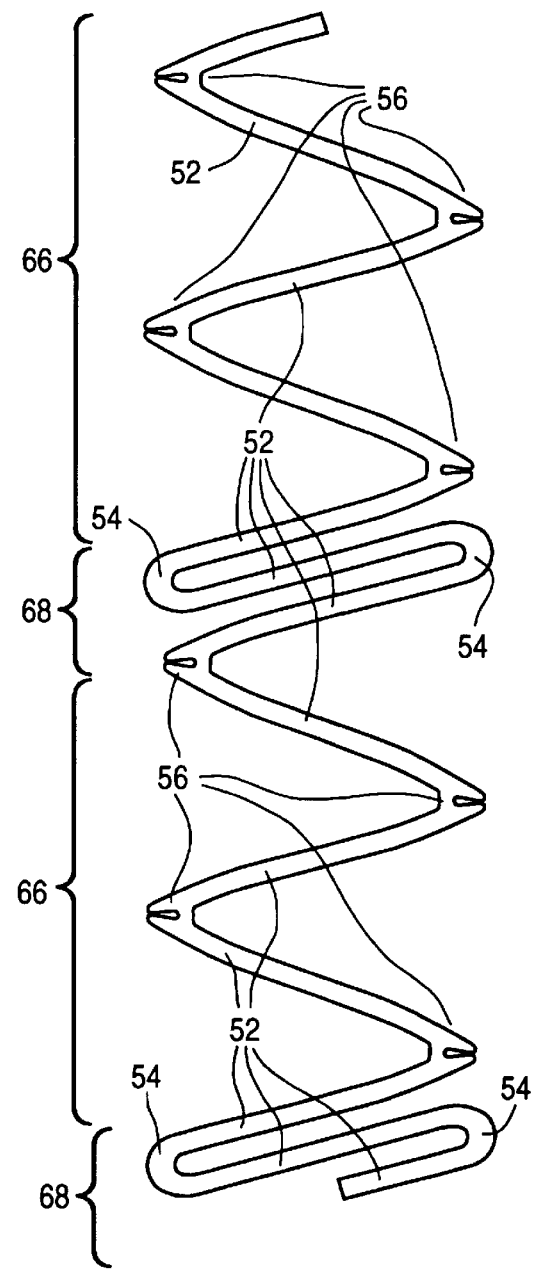
FIG. 11 illustrates the stent of FIG. 10, after partial deployment.
Figure 10A:
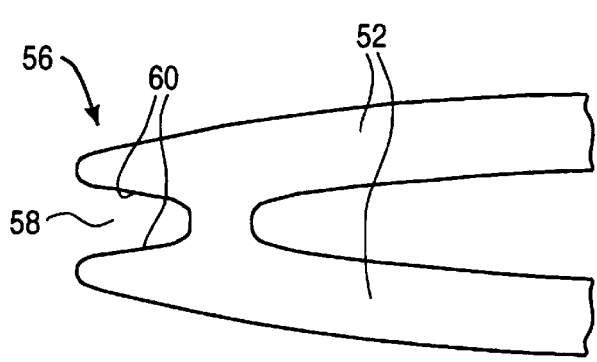

Yet another embodiment of a stent 50 constructed in accordance with the principles of the present invention is illustrated in FIGS. 10, 10A, and 11. The stent 50 is a zig-zag stent comprising struts 52 joined by hinge regions 54 and 56. The hinge regions 56 are weakened relative to hinge regions 54 by provision of a generally V-shaped notch 58, as illustrated in FIG. 10A. The notch 58 includes a pair of opposed stop surfaces 60 which act to prevent deflection of struts 52 beyond predetermined angular limit, as described generally above in connection with the embodiments of FIGS. 7–9. Partial deployment of the stent 50 is illustrated in FIG. 11 where a pair of evenly expanded regions 66 are uniformly arranged about a pair of non-expanded regions 68.

Figure 12:
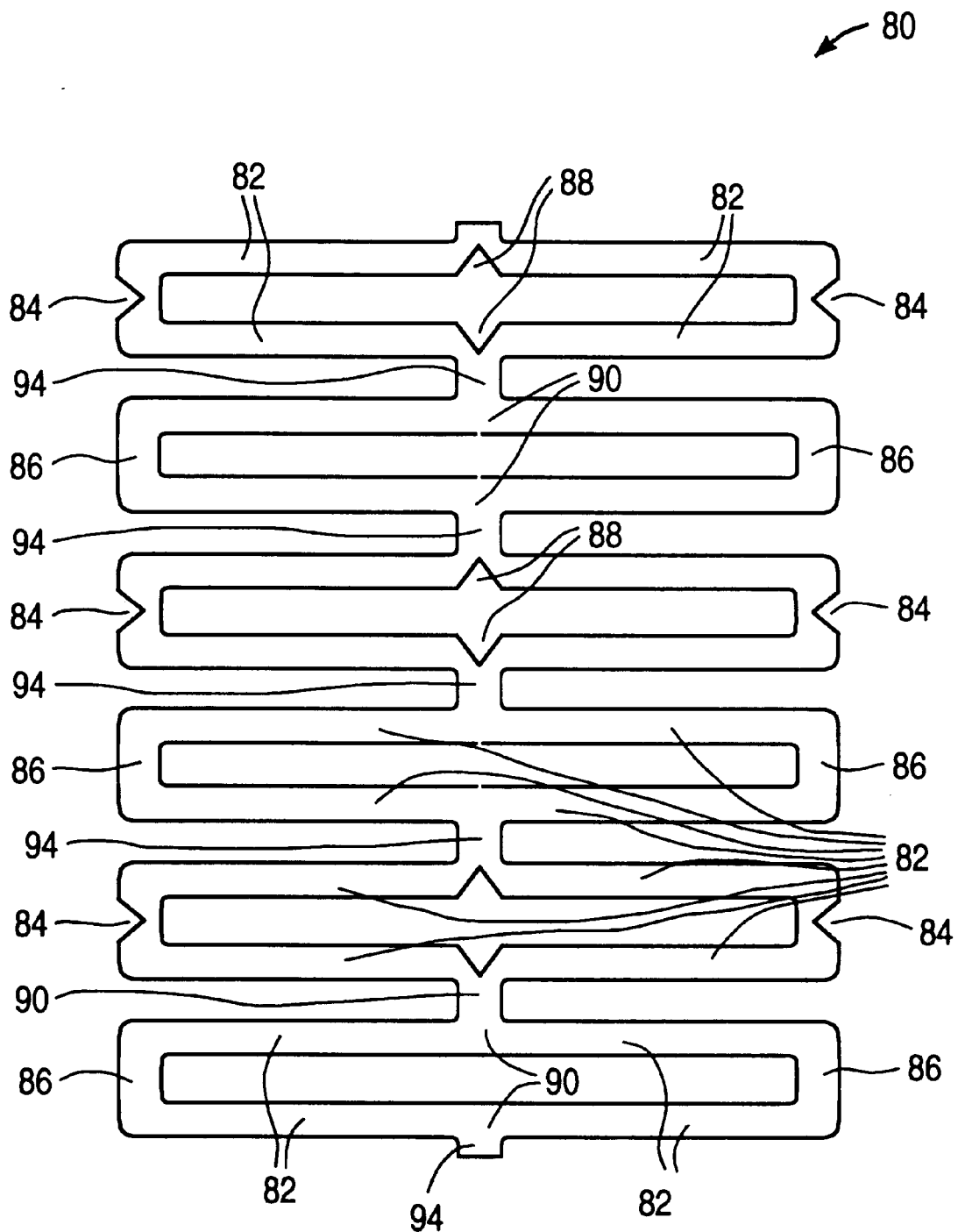
FIG. 12 illustrates yet another embodiment of a stent constructed in accordance with the principles of the present invention.
Figure 13:
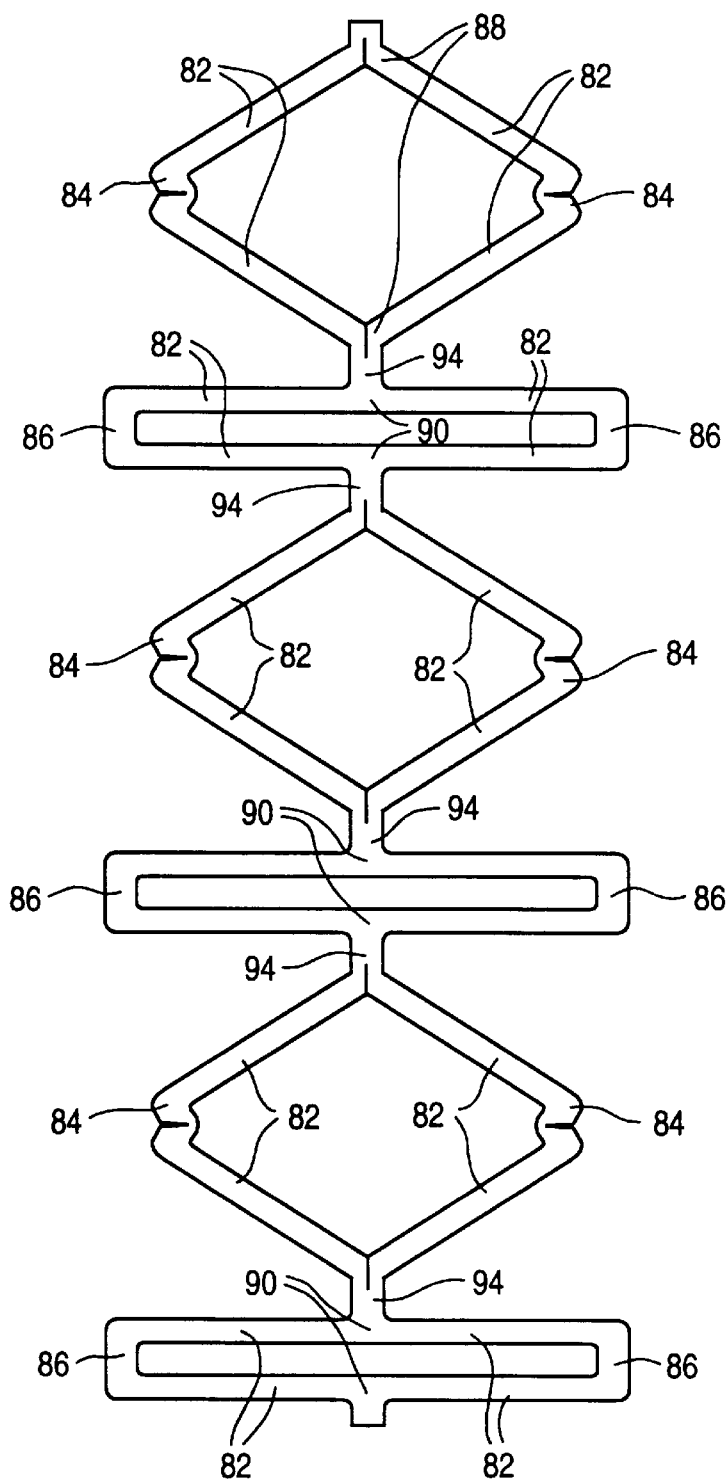
FIG. 13 illustrates the stent of FIG. 12 after partial deployment.

Referring now to FIGS. 12 and 13, yet another stent 80 constructed in accordance with the principles of the present invention will be described. The stent 80 includes a total of six box elements or structures, each including four struts 82 joined by four hinge regions. Certain of the box structures will be joined by weakened hinge regions 84 and 88, while others of the box structures will be joined by non-weakened hinge regions 86 and 90. Circumferentially adjacent box structures are joined by tabs 94 which exert a radially expansive force on the hinge regions 88 and 90 as the stent 80 is expanded. As best seen in FIG. 13, such a construction provides for initial yielding of the three of box structures having weakened hinge regions while the remaining box structures do not significantly expand at the onset.

Figure 14:
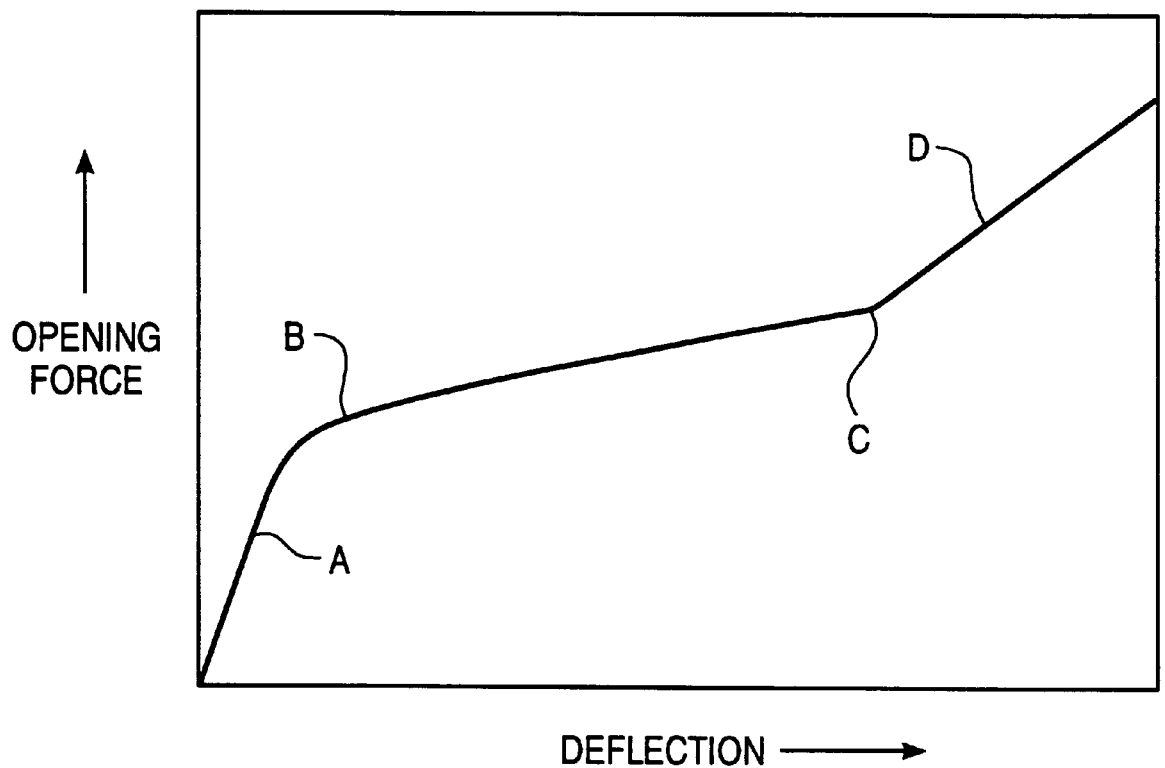
FIG. 14 is a graph illustrating the opening characteristics of the stent of FIGS. 12 and 13.

As shown in FIG. 13, the stent 80 is partially deployed, with the three box structures having weakened hinge regions being fully opened (i.e. opened to the extent that the opposed surfaces of the hinge regions 84 and 88 have closed) but with the other box structures remaining substantially unopened. As a radially expansive force continues to be applied to the stent 80, the remaining box structures will begin to deploy, but will require a greater radially expansive force than was required for opening the box structures having weakened hinge regions. The relationship between the opening force and the expansion of the stent 80 is illustrated in FIG. 14. FIG. 14 is an idealized graph showing the relationship between the opening force applied to a rolled-out stent structure, as shown in FIG. 12, and the overall deflection or degree of opening. In an initial phase of opening, shown as portion A of the figure, the box structures having weakened hinge regions will begin to open in an elastic manner. That is, over the initial opening or deflection, the opening will be elastic and the stent will return to its original configuration if the opening force is removed. After the opening force exceeds a certain level (shown as region B on the graph), expansion becomes plastic and non-reversible. The slope of the force (vs. deflection) required to yield the stent becomes smaller until the hinges 84 and 88 close, as shown in FIG. 13. At the point of closing, shown as region C on the graph, the slope of the force required to further open the stent 80 increases, as shown in region D of the graph. Such a greater force gradient is required to open the non-weakened box structures of the stent 80. It will be appreciated that the opening characteristics shown in FIG. 14 are idealized. For a real stent, slight differences in the opening characteristics of all of the hinge region 84, 86, 88, and 90, might result in a number of different stages showing as multiple near linear regions within the graph of FIG. 14.

Figure 15A:
FIGS. 15A and 15B illustrate the opening characteristics of a hinge region having a substantially uniform width.
Figure 15B:
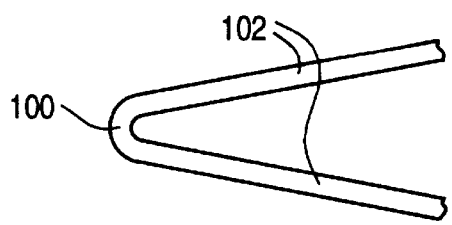

Referring now to FIGS. 15A–18B, a variety of hinge regions which may be employed in the stents and prostheses of the present invention will be described. In FIGS. 15A and 15B, a hinge region 100 joining a pair of adjacent struts 102 is illustrated. The hinge region 100 is shown as having a width and cross-sectional area which is the same as that for the adjacent struts 102. As an opening force is applied to the struts, the hinge region 100 will yield because of the stress concentration which occurs within the hinge region. It will be appreciated that the hinge region 100 may be considered either "weakened" or "non-weakened" within the definitions of the present invention depending on the nature of the other hinge region(s) within any particular stent or prosthesis structure. That is, the terms "weakened" and "non-weakened" are relative only and meant to assign the order of opening, with the weakened hinge regions opening before the non-weakened hinge regions.

Figure 16A:
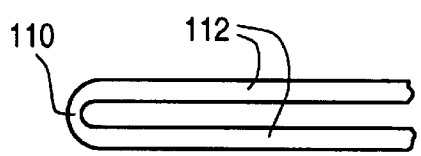
FIGS. 16A and 16B illustrate the opening characteristics of a hinge region having a narrowed width.
Figure 16B:
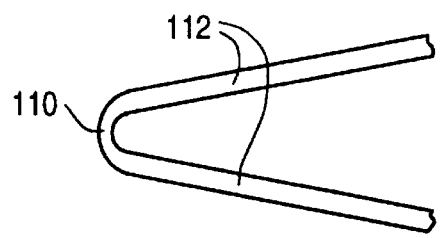

FIGS. 16A and 16B illustrate a hinge region 110 having a reduced width compared to the width of the adjacent struts 112. In an exemplary stent construction according to the present invention, the hinge regions 110 will be weakened hinge regions and the hinge regions 100 will be non-weakened hinge regions. It will be appreciated, however, that hinge regions 110 may be provided with different degrees of narrowing, resulting in a hierarchy of weakened and non-weakened hinge regions within any particular stent structure. Opening of the hinge region 110 will occur about a central point defined by the hinge region 110.

Figure 17A:
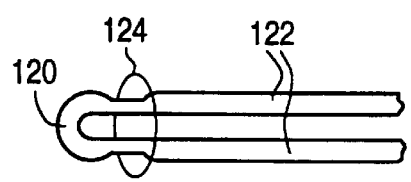
FIGS. 17A and 17B illustrate the opening characteristics of a first embodiment of a hinge region having a pair of opposed narrowed sections.
Figure 17B:
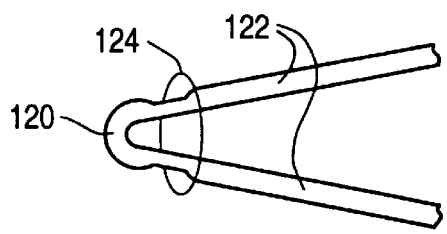

Another hinge region 120 is illustrated in FIGS. 17A and 17B. The hinge region 120 itself has a width which is generally the same as adjacent struts 122. The opening characteristics of the hinge region are defined by a pair of narrowed regions 124 which are located at the transition between the U-shaped apex of the hinge and the beams of the adjacent struts 122. As the struts 122 are opened, bending will occur preferentially in the narrowed regions 124, as shown in FIG. 17B. Some opening and bending may occur within the U-shaped portion of the hinge 120, although it will generally account for only a small portion of the opening of struts 122.

Figure 18A:
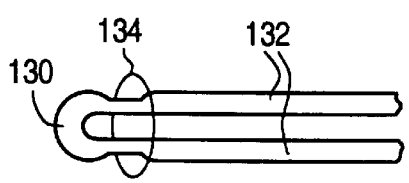
FIGS. 18A and 18B illustrate the opening characteristics of a second embodiment of a hinge region having a pair of opposed narrowed sections.
Figure 18B:
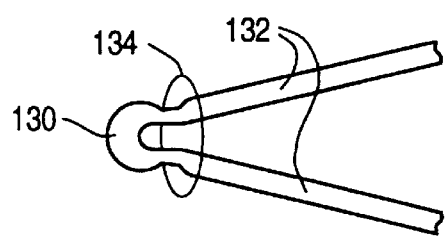

Yet another hinge region 130 is illustrated in FIGS. 18A and 18B. Hinge region 130 is similar to hinge region 120, except that the width of the U-shaped portion of the hinge is increased relative to the widths of the adjacent struts 132. Thus, substantially all bending will occur in the narrow regions 134, as shown in FIG. 18B.

In another aspect of the present invention, the prosthesis described above may be plated with radiopaque materials in order to adjust the radiopacity of the stent. The stents will be uniformly plated over their entire lengths, either on the inside, outside, or both sides of the body segments of the stent. Such plating is particularly desirable with stainless steel and other materials which are not inherently radiopaque. The radiopaque material should be biocompatible, preferably being a metal which can be electroplated onto the stent, more preferably being gold, platinum, tantalum, tungsten, or alloys thereof. The material should be plated until sufficient radiopacity has been imparted so that the stents are observable under conventional fluoroscopy, but preferably permitting some fluoroscopic visibility through the stent. For gold, the optimum thicknesses are in the range from 0.01 mm to 0.03 mm.

Although the foregoing invention has been described in some detail by way of illustration and example, for purposes of clarity of understanding, it will be obvious that certain changes and modifications may be practiced within the scope of the appended claims.

What is claimed is:

1. A radially expansible tubular prosthesis comprising at least one serpentine element having struts or box element having struts, wherein said struts are joined together by hinge regions which yieldably open in a circumferential direction in response to a radially outwardly directed internal force, wherein selected ones of the hinge regions are weakened relative to others of the hinge regions so that said selected ones of the hinge regions will begin to open before said others of the hinge regions begin to open, wherein the prosthesis includes a plurality of said weakened hinge regions which are distributed evenly about a periphery of the prosthesis so that the prosthesis opens in a more uniform manner.

2. A prosthesis as in claim 1 wherein the tubular prosthesis comprises a serpentine element and the struts have substantially equal lengths and are arranged in a reversing pattern.

3. A prosthesis as in claim 2, wherein the reversing pattern is a repeating S-shaped pattern.

4. A prosthesis as in claim 2, wherein the reversing pattern is a repeating Z-shaped pattern.

5. A prosthesis as in claim 1, comprising box elements wherein each box element includes four struts joined by four hinges.

6. A prosthesis as in claim 5, wherein prior to expansion the struts are disposed in two colinear pairs with two hinge regions between each of the struts of the colinear pairs and two hinges between ends of each pair to form a box and subsequent to expansion the box transforms to a diamond pattern.

7. A prosthesis as in claim 1, wherein at least some of the hinge regions which are weakened are located between adjacent ends of a pair of struts.

8. A prosthesis as in claim 1, wherein at least some of the hinge regions which are weakened comprise pairs of narrowed sections adjacent pair of struts.

9. A prosthesis as in claim 1, wherein said selected ones of the hinge regions have a width that is reduced relative to widths of said others of the hinge regions.

10. A prosthesis as in claim 9, wherein selected ones of the hinge regions have widths which are reduced by from 20% to 30% relative to widths of the others of the hinge regions.

11. A prosthesis as in claim 1, wherein at least some of the hinge regions include opposed stops which engage each other as the hinge region is opened and which inhibit further opening after they engage each other.

12. A prosthesis as in claim 11, wherein the hinge regions have a C-shaped pattern.

13. A prosthesis as in claim 11, wherein the hinge regions have a generally V-shaped pattern.

14. A prosthesis as in claim 2, wherein the serpentine element extends about a full circumference of the tubular prosthesis and wherein the hinge regions which are weakened are distributed in a pattern that results in a plurality of equally circumferentially spaced-apart segments opening prior to segments therebetween.

15. A method for delivering a radially expansible tubular prosthesis to a body lumen, said method comprising:

providing a prosthesis as in claim 1; and applying a radially outward force within a lumen of the prosthesis to radially expand said prosthesis, wherein said hinge regions which are weakened yield before other hinge regions.

* * * * *